United States Patent [19]

Gaudette et al.

[11] 3,988,360

[45] *Oct. 26, 1976

[54] PROCESS FOR PREPARING IMINODIACETONITRILE

[75] Inventors: Roger Robert Gaudette; James Edward Philbrook, both of Nashua; Jon Carl Thunberg, Amherst, all of N.H.

[73] Assignee: W. R. Grace & Co., Columbia, Md.

[ * ] Notice: The portion of the term of this patent subsequent to Sept. 9, 1992, has been disclaimed.

[22] Filed: Sept. 8, 1975

[21] Appl. No.: 611,369

Related U.S. Application Data

[63] Continuation-in-part of Ser. No. 416,026, Nov. 15, 1973, Pat. No. 3,904,668.

[52] U.S. Cl. ........................................ 260/465.5 A
[51] Int. Cl.² ........................................ C07C 120/00
[58] Field of Search .............. 260/465.5 A, 465.5 R

[56] References Cited
UNITED STATES PATENTS

3,904,668  9/1975  Gaudette et al. ............ 260/465.5 A

OTHER PUBLICATIONS

Rodd, "Chemistry of Carbon Compounds," vol. 1, Part B, 1952, p. 804.

*Primary Examiner*—Joseph Paul Brust
*Attorney, Agent, or Firm*—Elton Fisher

[57] ABSTRACT

Iminodiacetonitrile is prepared by a process comprising: (a) forming an aqueous reaction mixture by admixing water, hexamethylenetetramine, formaldehyde, and HCN; and (b) forming iminodiacetonitrile by passing the aqueous reaction mixture through a continuous reaction zone while maintaining the temperature within the continuous reaction zone at 50°–250° C. The resulting iminodiacetonitrile can be recovered or it can be hydrolyzed to form an alkali metal salt of iminodiacetic acid which can be recovered or converted to iminodiacetic acid which can be recovered.

In other embodiments: (a) the hexamethylenetetramine solution and the formaldehyde solution can be combined before being admixed with the HCN; or (b) the formaldehyde solution and the HCN can be admixed with a stabilizing acid to form an acid stabilized aqueous solution of formaldehyde and HCN before being admixed with the hexamethylenetetramine solution in the reaction zone in which iminodiacetonitrile is formed.

9 Claims, No Drawings

PROCESS FOR PREPARING IMINODIACETONITRILE

CROSS REFERENCE TO RELATED APPLICATIONS

This is a continuation-in-part of our copending application Ser. No. 416,026, filed Nov. 15, 1973, and now U.S. Pat. No. 3,904,668, the specification of which is incorporated herein by reference.

BACKGROUND OF THE INVENTION

This invention is in the field of iminodiacetonitrile (IDAN) preparation. More particularly it is directed to a process for preparing IDAN by reacting hexamethylenetetramine, formaldehyde, and HCN in an aqueous reaction medium (an aqueous reaction mixture). Even more specifically, this invention is directed to a continuous process in which said aqueous reaction mixture is passed through a continuous reaction zone (e.g., a tubular reactor, a continuous overflow autoclave, or the like) to form IDAN.

It was reported over 80 years ago that IDAN is obtained in an unspecified yield by reacting hydrogen cyanide with HMTA. Eschweiler, Ann., 278, 229–239, (1894). Later, in 1921, Dubsky et al, Ber., 54, 2659, confirmed that IDAN can be formed by reacting HMTA with aqueous hydrogen cyanide. In 1957, in U.S. Pat. No. 2,794,044, Miller disclosed the preparation of IDAN in a yield of about 65% by reacting ammonia, formaldehyde and hydrogen cyanide in an aqueous acid solution having a pH of 5.5 to 6.5. More recently, in U.S. Pat. No. 3,167,580, Saunders et al showed in examples that IDAN is obtained rapidly in a continuous process comprising bringing into reactive contact acid stabilized formaldehyde and hydrogen cyanide mixture and ammonia under carefully controlled reactant ratios and temperatures and at a pH of greater than 7 using a continuous reaction zone (a tubular reactor).

Stutts, U.S. Pat. No. 3,412,137, teaches a process for preparing IDAN by reacting an aqueous solution of HMTA and HCN in an aqueous medium buffered at a pH of about 5–6.5

Philbrook et al, U.S. Pat. No. 3,886,198, teach a process for preparing IDAN which comprises forming an aqueous mixture of HMTA, HCN, and a strong acid and continuously passing said mixture (which has an acidic pH — e.g., a pH of 3–5) through a tubular reactor at about 50°–120° C to form the desired IDAN.

Sexton, U.S. Pat. No. 2,895,989, teaches the conversion of IDAN to an alkali metal salt of iminodiacetic acid (i.e., to IDAM) by hydrolyzing the IDAN with an alkali metal hydroxide. Sexton also teaches the conversion of such salt to iminodiacetic acid (IDA).

SUMMARY OF THE INVENTION

In summary, this invention is directed to a continuous process for preparing IDAN comprising:

a. continuously preparing an aqueous reaction mixture comprising or consisting essentially of HMTA, formaldehyde, and HCN having a mole ratio of HMTA to formaldehyde to HCN of 1:1–2.2:6.9–8.6 in a continuous reaction zone by continuously feeding an aqueous HMTA solution having a temperature of 0°–80° C, an aqueous formaldehyde solution having a temperature of 0°–80° C, and HCN having a temperature of 0°–25° C, into the continuous reaction zone, the pH of the resulting aqueous reaction mixture being 5–10;

b. preparing an aqueous system containing the IDAN by continuously passing the aqueous reaction mixture through the continuous reaction zone while maintaining the temperature within the continuous reaction zone at 50°–250° C, residence time in the continuous reaction zone being 0.05–20 minutes; and c. continuously recovering the IDAN exit the continuous reaction zone.

DESCRIPTION OF PREFERRED EMBODIMENTS

In preferred embodiments of the above Summary:

1. The temperature within the continuous reaction zone is 120°–170° C.
2. The residence time within the continuous reaction zone is 0.1–5 minutes.
3. The pH of the aqueous reaction mixture is 6.5–9.5.
4. The aqueous system exit the continuous reaction zone is cooled to 0°–40° C to cause the iminodiacetonitrile to separate therefrom.
5. The mole ratio of HMTA to formaldehyde to HCN is 1:1.6–2.2:7.2–8.0.
6. The mole ratio of HMTA to formaldehyde to HCN is 1:1.8:7.6.

In another preferred embodiment ("Embodiment A") this invention is directed to a continuous process for preparing IDAN comprising:

a. continuously preparing an aqueous reaction mixture of HMTA, formaldehyde, and HCN having a mole ratio of HMTA to formaldehyde to HCN of 1:1–2.2:6.9–8.6 by continuously admixing the HCN and an aqueous solution of the HMTA and the formaldehyde in a continuous reaction zone, the temperature of the HCN being 0°–25° C and the temperature of the aqueous solution of the hexamethylene tetramine and the formaldehyde being 0°–80° C, the pH of the aqueous reaction mixture being 5–10;

b. continuously preparing an aqueous system containing the IDAN by passing the aqueous reaction mixture through the continuous reaction zone while maintaining the temperature within the continuous reaction zone at 50°–250° C, residence time in the continuous reaction zone being 0.05–20 minutes; and c. continuously recovering the IDAN exit the tubular reaction zone.

In other embodiments of our invention as recited in Embodiment A:

1. The temperature within the continuous reaction zone is maintained at 120°–170° C while passing the aqueous reaction mixture through the continuous reaction zone.
2. The residence time in the continuous reaction zone is 0.1–5 minutes.
3. The pH of the aqueous reaction mixture is 6.5–9.5.
4. The aqueous system exit the continuous reaction zone is cooled to 0°–40° C to cause the IDAN to separate therefrom.
5. The mole ratio of HMTA to formaldehyde to HCN is 1:1.6–2.2:7.2–8.0.

The aqueous solution of HMTA and formaldehyde used in Embodiment A can be prepared by admixing an aqueous formaldehyde solution with an aqueous HMTA solution in a mixing and storage zone. If desired two mixing and storage zones can be used. In an operation using two mixing and storage zones the aqueous solution of HMTA and formaldehyde can be prepared in one (a first mixing and storage zone) while feeding a previously prepared aqueous solution from another (a second mixing and storage zone). When the second mixing and storage zone becomes empty (or nearly empty), it can be replaced with the filled first mixing and storage zone from which the aqueous solution of HMTA and formaldehyde contained therein can be fed to the continuous reaction zone while preparing a new lot of said aqueous solution in the now empty (or nearly empty) first mixing and storage zone. By feeding from one mixing and storage zone while charging (preparing) a new lot of said aqueous solution in the other, continuous runs of long duration can be made without interrupting feed of the aqueous solution of HMTA and formaldehyde to the continuous reaction zone.

The concentration of HMTA and formaldehyde in the aqueous solution of HMTA and formaldehyde is not critical. However said solution generally contains about 5–30% HMTA. The mole ratio of HMTA to formaldehyde in said solution — which is generally prepared from an aqueous formaldehyde solution containing 30-50% formaldehyde — should be 1:1–2.2.

In another preferred embodiment ("Embodiment B") this invention is directed to a continuous process for preparing IDA comprising:

a. continuously preparing an aqueous reaction mixture of hexamethylenetetramine, formaldehyde, and HCN having a mole ratio of HMTA to HCHO to HCN of 1:1–2.2:6.9–8.6 by continuously admixing an aqueous hexamethylenetetramine solution and an acid stabilized aqueous admixture (solution) of formaldehyde and HCN in a continuous reaction zone, the pH of the aqueous reaction mixture being 5–10;

b. continuously preparing an aqueous system containing the iminodiacetonitrile by passing the aqueous reaction mixture through the continuous reaction zone while maintaining the temperature within the continuous reaction zone at 50°–250° C, residence time in the continuous reaction zone being 0.05-20 minutes; and c. continuously recovering the iminodiacetonitrile exit the continuous reaction zone.

In other embodiments of our invention as set forth in Embodiment B, supra:

1. The temperature within the continuous reaction zone is maintained at about 120°–170° C while passing the aqueous reaction mixture through the continuous reaction zone.

2. The residence time in the continuous reaction zone is 0.1–5 minutes.

3. The pH of the aqueous reaction mixture is 6.5–9.5.

4. The aqueous system exit the continuous reaction zone is cooled to 0–40° C to cause the iminodiacetonitrile to separate therefrom.

5. The mole ratio of hexamethylenetetramine to formaldehyde to HCN is 1:1.6–2:7.2–8.0.

The acid stabilized aqueous mixture of formaldehyde and HCN of Embodiment B can be prepared by admixing a stabilizing acid and an aqueous formaldehyde solution with HCN in a mixing and storage zone. If desired, two mixing and storage zones can be used. In an operation using two mixing and storage zones the acid stabilized aqueous mixture can be prepared in one (a first mixing and storage zone) while feeding a previously prepared acid stabilized mixture from another (a second mixing and storage zone). When the second mixing and storage zone becomes empty (or nearly empty), it can be replaced with the filled first mixing and storage zone from which the acid stabilized aqueous mixture of formaldehyde and HCN contained therein can be fed to the continuous reaction zone while preparing a new lot of said acid stabilized mixture in the now empty (or nearly empty) first mixing and storage zone. By feeding from one mixing and storage zone while charging (preparing) a new lot of acid stabilized mixture in the other, continuous runs of long duration can be made without interrupting feed of the acid stabilized aqueous mixture of formaldehyde and HCN to the continuous reaction zone.

Where preparing the acid stabilized aqueous mixture of formaldehyde and HCN sufficient acid (e.g., $H_2SO_4$, or HCl, $H_3PO_4$, or the like) is included in the mixture to cause it to preferably have a pH of about 1 or 2. The pH is not critical so long as it is about 1 or 2 or somewhat lower or somewhat higher (e.g., below about 4). An amount of acid effective for forming an acid stabilized aqueous admixture of formaldehyde and HCN is included in the mixture. Such amount of acid causes the acid stabilized aqueous admixture of formaldehyde and HCN to have a pH within the above-mentioned range. The concentration of the formaldehyde solution used is not critical and is generally about 30–50%. Neither is the concentration of HCN and formaldehyde in the acid stabilized mixture of formaldehyde critical, however the mole ratio of formaldehyde to HCN should be about 1–2.2:6.9–8.6. In general, the formaldehyde concentration in said acid stabilized mixture is about 5–30%.

Admixing the aforesaid acid stabilized mixture of formaldehyde and HCN with HMTA solution to form the aqueous reaction mixture of Embodiment A results in the formation of an aqueous reaction mixture having a pH between 5 and 10.

DETAILED DESCRIPTION OF THE INVENTION

As noted supra, Miller's U.S. Pat. No. 2,794,044 teaches a process for preparing IDA. The Miller reference states correctly that:

The obvious equation for the reaction producing iminodiacetonitrile is:

When, however, the reactants are mixed in the stoichiometric ratio demanded by this equation, no product can be isolated regardless of the pH adjustment. The following different equation expresses the stoichiometric ratios necessary to obtain the best yield, ca. 65%: $4NH_3 + 2CH_2O + 6HCN[H^+]3HN(CH_2CN)_2 + NH_3 + 6H_2O$ Since $NH_3$ and $CH_2O$ in this ratio yields HMTA, and if $H_2SO_4$ is used to neutralize the $NH_3$ as it is formed, an equivalent equation would be:

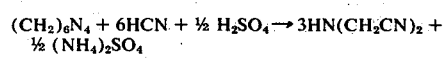

This equation illustrates several disadvantages of said method of IDAN manufacture; only ¾ of the N in the HMTA is converted to IDAN, the remaining ¼ is released as $NH_3$ (i.e. as $(NH_4)_2SO_4$). Consequently, the HMTA is not used efficiently. The release of $NH_3$ requires constant pH control by the addition $H_2SO_4$. The product is thus a slurry of IDAN crystals in a liquor containing dissolved IDAN, HCN, other organic byproducts, and large amounts of $(NH_4)_2SO_4$. In practice, this liquor cannot be recycled; it must, therefore, receive costly effluent treatment before it can be discharged.

We have found that IDAN can be prepared from HMTA, formaldehyde, and HCN according to the following equation:

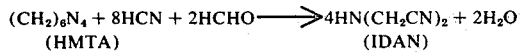

$$(CH_2)_6N_4 + 8HCN + 2HCHO \longrightarrow 4HN(CH_2CN)_2 + 2H_2O$$
(HMTA)                                           (IDAN)

Such a procedure avoids the above problems. Since no $NH_3$ is released, all the HMTA is potentially available for conversion to IDAN and no $H_2SO_4$ is required. Thus, higher yields can be obtained, close pH control is not needed, and the formation of intermediate glycolonitrile (the intermediate used in our aforesaid application Ser. No. 416,026) is avoided. The process can therefore readily be made continuous. Furthermore, since the product is essentially IDAN with no inorganic contamination, the reaction mixture in its entirety can be hydrolyzed with alkali metal hydroxide to give $IDAM_2$. When this is done, the effluent problem is totally eliminated. If IDAN is the desired product, it can be crystallized from the reaction product. The resulting liquor would be free of $(NH_4)_2SO_4$ and, therefore could be hydrolyzed with NaOH to give useful $IDANa_2$ without the production of sodium sulfate — an undesirable side product.

Where hydrolyzing IDAN to $IDANa_2$ (or $IDAK_2$) the ammonia which is produced is recovered. It (the ammonia) can be used as fertilizer (e.g., as ammonium sulfate or ammonium phosphate); alternatively, the recovered ammonia can be converted to HMTA and/or HCN and recycled into the process. Other uses for the recovered ammonia will be readily apparent to those skilled in the art.

Conveniently, the continuous reaction zone used in the process of this invention can be surrounded by a heat enchange medium (e.g., oil, Dowtherm, chlorinated hydrocarbons, steam or the like) maintained at a predetermined temperature to provide heating or cooling, if required. Alternatively, electrical heating can be used to maintain a predetermined temperature within the reaction zone if heating is required. Still other temperature control methods will be readily apparent to those skilled in the art.

The aqueous system (reacted mixture containing product IDAN) exit the continuous reaction zone can be cooled by passing it (the aqueous system) through a heat exchanger or by placing it in a tank or vessel provided with cooling coils or a cooling jacket. Other methods for cooling said aqueous system will be readily apparent to those skilled in the art.

The IDAN product, which is a solid, can be separated from the cooled aqueous mixture (aqueous system) exit the tubular reactor by centrifugation, decantation, or filtration.

Alternatively the aqueous system exit the tubular reaction zone can be fed into an alkali metal hydroxide solution and hydrolyzed directly to alkali metal iminodiacetate ($IDAM_2$).

Where operating at temperatures (in the continuous reactor) above about 100° C a pressure in excess of atmospheric pressure (760 Torr) is maintained on the mixture (aqueous system) in the reaction zone to prevent excessive vaporization in the reactor (continuous reaction zone).

The weight ratio of water to reactants (HMTA, formaldehyde, and HCN) can be varied over wide limits. Weight ratios of water to reactants as high as 10:1 or higher produce excellent results, and excellent results can also be obtained where using just enough water to maintain a solution (a one phase system) in the mixing zone (e.g., Tee or cross) and in the continuous reaction zone.

In the process of our invention as set forth in the Summary and in the preferred embodiments, the continuous reaction zone can be a tubular reactor, a continuous outflow (e.g., continuous overflow) autoclave, or the like.

Where using a tubular reactor, a mixing cross and/or one or more mixing Tees (depending on the number of feed streams being fed into the reactor) can comprise an inlet and mixing zone which is a part of the reactor, and the feed streams can be mixed in such mixing cross and/or mixing Tee(s) which comprise a part of the reactor.

Where using a continuous outflow autoclave, reactant feed streams can be fed into the autoclave and admixed therein by mixing means provided within the autoclave. Alternatively, a mixing cross and/or one or more mixing Tees can be attached to the autoclave to comprise an inlet to the autoclave, and the feed streams can be mixed in such mixing cross and/or mixing Tee(s) which comprise a part of the reactor.

Where using a mixing cross and at least one mixing Tee or where using more than one mixing Tee, the cross and Tee(s) or the Tees are connected in series so that discharge from the discharge arm of one constitutes feed into a feed receiving arm of the other.

The methods set forth in: (a) the above Summary; (b) Embodiment A; and (c) Embodiment B are fully equivalent and produce fully equivalent results. In other words, Embodiments A and B constitute fully equivalent variations of the method set forth in said Summary.

The concentrations of the solutions used in forming the aqueous reaction mixture in the process of our invention are not critical. However, we generally prefer to use an aqueous formaldehyde solution containing about 30–50% HCHO and an aqueous HMTA solution containing about 10–30% HMTA. HCN can be supplied as an aqueous HCN solution containing about 20–99% HCN, as HCN vapor, or preferably as anhydrous liquid HCN.

The instant invention will be better understood by referring to the following specific but nonlimiting examples and procedures. It is understood that said invention is not limited by these examples and procedures which are offered merely as illustrations; it is also understood that modifications can be made without departing from the spirit and scope of the invention.

The examples were actually run.

The procedures, while not actually run, will further illustrate the preparation of IDAN by certain embodiments of the process of our invention.

EXAMPLE 1

An aqueous solution of HMTA and formaldehyde containing 14.2% HMTA and having a mole ratio of HMTA to formaldehyde of 1:1.95 was prepared. This solution and HCN were pumped simultaneously with separate metering pumps into a mixing Tee at the head (inlet) of a continuous tubular reactor. The mole ratio of HMTA to HCN was maintained at 1:7.78.

The continuous reactor was constructed of ten sections of ⅛ inch × 10 foot jacketed steel pipe, followed by three sections of ⅛ inch × 20 foot unjacketed steel pipe, the sections being connected in series. At the end of each section was mounted a thermocouple and a sample valve. Temperature of the mixture within the reactor was controlled at 140° C by passing steam at 40 pounds per square inch gauge pressure (psig) through the jacket. Pressure within the continuous reactor was controlled at 200–250 psig with an adjustable pressure relief valve.

Weighed samples of the nitrile product were collected at various sample valves and saponified with sodium hydroxide solution. The saponified samples were analyzed by silylation-gas chromotography for glycine, IDA, and nitrilotriacetic acid (NTA). The saponified samples were also titrated with standard copper(II) chloride solution. The results obtained are reported in Table I, infra.

EXAMPLE 2

The general method of Example 1 was repeated but at other temperatures, residence times, and mole ratios. In this instance samples were taken only from the first sample point at which the reaction was complete (i.e., at the minimum residence time at which reaction was complete). The results obtained are presented in Table II, infra.

EXAMPLE 3

The general method of Example 2 was repeated, but in this instance the aqueous solution of HMTA and formaldehyde was heated prior to being fed into the continuous reactor (continuous reaction zone) in which it (the aqueous solution of HMTA and formaldehyde) was admixed with the HCN. In this example the first two sections of the continuous reactor were unheated, but steam was applied to the next eight sections as in Example 1. The results obtained are shown in Table III, infra.

Saunders et al (U.S. Pat. No. 3,167,580) reported that product mixtures of IDAN and glycinonitrile are obtained where preparing IDAN by the reaction of formaldehyde, HCN, and ammonia. Their product sometimes contains small amounts of N-methyleneglycinonitrile.

We have found that glycinonitrile and a small amount of NTAN are formed as side products where preparing IDAN by the process of our invention.

We have also found (see Table II) that the ratio of glycinonitrile to IDAN in the product exit our continuous reaction zone can be increased by adjusting the mole ratio of the reactants (HMTA, formaldehyde, and HCN). This technique is especially useful where both IDA and glycine are desired as final products because IDAN rich in glycinonitrile can be prepared, converted to the $H_2NCH_2COONa$ and $IDANa_2$ which can, in turn, be converted to glycine and IDA. The glycine and IDA can be separated by crystallization from an aqueous solution, and recovered separately.

Thus (see Run No. 8 in Table II) a product yielding (as an upper limit) about 14% glycine and (as a lower limit) about 84% IDA was obtained by feeding the reactants in a mole ratio of HMTA to HCHO to HCN of 1:1:6.95 while a product exit the continuous reaction zone which was considerably richer in glycinonitrile and considerably poorer in IDAN was obtained by adjusting the mole ratio of said reactants to 1:0–1:6.82 and 1:0:5.93, respectively. See Runs Nos. 9 and 10 in Table II).

A mole ratio of HMTA-HCHO:HCN of about 1:0:5.4 will produce a still higher ratio of glycinonitrile to IDAN in the product exit the continuous reaction zone.

TABLE I

IDAN PREPARATION AT 140° C (1)
(Mole Ratio In Aqueous Reaction Mixture, HMTA:HCHO:HCN Is 1:1.95:7.78)

| Residence Time, Minutes | 0.2 | 0.4 | 0.6 | 1.3 | 1.6 | 2.1 | 4.0 |
|---|---|---|---|---|---|---|---|
| % Reaction (2) | 94 | 96 | 96 | 96 | 97 | 97 | 99 |
| Product Composition (3) | | | | | | | |
| IDA | (5) | (5) | 63% | 78% | 83% | 83% | 90% |
| Glycine | (5) | (5) | 33% | 19% | 15% | 14% | 7% |
| NTA | (5) | (5) | 3% | 3% | 3% | 4% | 3% |
| Yield of IDA (4) | (6) | (6) | 49% | 66% | 74% | 77% | 91% |

(1) The pH of the aqueous reaction mixture was 6.9.
(2) % of total HCN consumed.
(3) % of contained acids (the nitrile product was hydrolyzed with sodium hydroxide solution and analyzed; the results were reported as % IDA, % Glycine, and % NTA).
(4) Based on HCN charged.
(5) Not analyzed.
(6) Not calculated.

TABLE II

IDAN PRODUCTION

| Run No. | Mole Ratio HMTA:HCHO:HCN | Average Reaction Temperature, ° C | Res. Time, Minutes | % IDA | % Glycine | % NTA | IDA Yield (2) |
|---|---|---|---|---|---|---|---|
| 1 | 1.00:1.95:7.72 | 140 | 1.5 | 89 | 8 | 5 | 85 |
| 2 | 1.00:1.95:7.38 | 140 | 1.5 | 89 | 8 | 3 | 93 |
| 3 | 1.00:1.93:7.73 | 140 | 1.5 | 89 | 7 | 4 | 91 |
| 4 | 1.00:1.93:7.58 | 140 | 1.5 | 89 | 6 | 4 | 91 |
| 5 | 1.00:1.60:7.45 | 140 | 1.5 | 85 | 10 | 5 | 85 |
| 6 | 1.00:1.60:7.35 | 140 | 1.5 | 89 | 9 | 2 | 90 |
| 7 | 1.00:1.60:7.27 | 140 | 1.5 | 88 | 10 | 2 | 85 |
| 8 | 1.00:1.00:6.95 | 140 | 1.5 | 84 | 14 | 2 | 81 |
| 9 | 1.00:1.00:6.82 (3) | 140 | 1.5 | 73 | 24 | 4 | 60 |

TABLE II-continued

IDAN PRODUCTION

| Run No. | Mole Ratio HMTA:HCHO:HCN | Average Reaction Temperature, °C | Res. Time, Minutes | Composition of Product (1) % IDA | % Glycine | % NTA | IDA Yield (2) |
|---|---|---|---|---|---|---|---|
| 10 | 1.00:0:5.93 (3) | 125 | 1.5 | 65 | 33 | 2 | 60 |

(1) The nitrile product was hydrolyzed with sodium hydroxide and analyzed; the results were reported as % IDA, % Glycine, and % NTA.
(2) Based on HCN charged.
(3) Runs 9 and 10 illustrate a process in which the product exit the continuous reaction zone is rich in both IDAN and glycinonitrile.

TABLE III

IDAN PRODUCTION

| Run No. | Mole Ratio, HMTA:HCHO:HCN | Temperature of Aqueous Solution of HMTA and HCHO, °C | Average Reaction Temperature, °C | Res. Time, Minutes | Composition of Product (1) % IDA | % Glycine | %NTA | IDA Yield (2) |
|---|---|---|---|---|---|---|---|---|
| 1 | 1.00:1.84:7.58 | 40 | 130 | 2.5 | 90 | 7 | 3 | 90 |
| 2 | 1.00:1.84:7.58 | 67 | 130 | 2.5 | 88 | 8 | 4 | 89 |
| 3 | 1.00:1.84:7.20 | 40 | 130 | 2.5 | 84 | 13 | 3 | 84 |
| 4 | 1.00:1.84:7.71 | 44 | 150 | 1.2 | 88 | 8 | 4 | 89 |

(1) The nitrile product was hydrolyzed with sodium hydroxide and analyzed; the results were reported as % IDA, % Glycine, and % NTA.
(2) Based on HCN charged.

PROCEDURE 1

The method of Example 1 can be carried out by separately metering the aqueous HMTA solution, the aqueous formaldehyde solution, and the HCN into the continuous reaction zone (continuous reactor) using mole ratios of HMTA to formaldehyde to HCN of 1:1–2.2:6.9–8.6 or 1:1.6–2.2:7.2–8.0. Such procedure will produce IDAN in a conversion of about 85–90% based on the HCN charged.

PROCEDURE 2

The method of Example 1 can be carried out by first preparing an acid stabilizer aqueous mixture (solution) of formaldehyde and HCN by admixing an aqueous solution of formaldehyde, HCN, and an amount of an acid (e.g., HCl, $H_2SO_4$, $H_3PO_4$, or the like) to produce the acid stabilized aqueous solution of formaldehyde and HCN. Said solution will generally have a pH of about 1–4, or 1–2, or 2–3, or 3–4. The mole ratio of formaldehyde to HCN in such solution should be about 1–2.2:6.9–8.6 or 1.6–2.2:7.2–8.0 This solution and an aqueous HMTA solution can be separately metered into the continuous reactor to provide a mole ratio of HMTA to formaldehyde to HCN of 1:1–2.2:6.9–8.6 or 1:1.6–2.2:7.2–8.0. IDAN will be produced in a yield of about 85–90% of theory based on the HCN charged.

IDAN is an intermediate on a route to IDA which can be prepared from IDAN by a method taught by Eschweiler (Ann. 1894, 278, 229–239). IDA is used in metal plating baths. German Pat. No. 1,034,946 (Chem. Abstracts 1960, 54, 16237e) teaches the use of IDA in cyanide-containing copper (and copper alloy) plating baths. The presence of IDA in such baths causes copper (or the copper alloy) to plate (precipitate) as a bright coating.

The use of IDA in the preservation of rubber latex is taught by British Pat. No. 800,089 (Chem. Abstracts 1959, 53, 2672i).

When heated in an aqueous medium with about a stoichiometric quantity of sodium hydroxide solution IDAN yields disodium iminodiacetate (IDANa₂) according to the following equation:

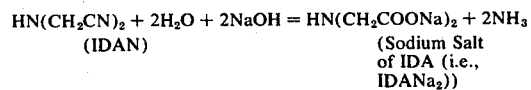

$$HN(CH_2CN)_2 + 2H_2O + 2NaOH = HN(CH_2COONa)_2 + 2NH_3$$
(IDAN)       (Sodium Salt of IDA (i.e., IDANa₂))

French Pat. No. 1,190,714 (Chem. Abstracts 1960, 54, 25993g) teaches the use of IDANa₂ as an agent for removing residual catalyst (e.g., Ti, Cr, Fe, V, or Al salts) from polyolefins.

As used herein the term "percent(%)" means parts per hundred and parts means parts by weight unless otherwise defined where used.

The term "mole" has its generally accepted meaning, i.e., a mole of a substance is that quantity which contains the same number of molecules of the substance as there are atoms in 12 grams of pure $^{12}C$.

As used herein the term:
a. "IDA" means iminodiacetic acid.
b. "IDAN" means iminodiacetonitrile.
c. "NTA" means nitrilotriacetic acid.
d. "NTAN" means nitrilotriacetonitrile.
e. "HMTA" means hexamethylenetetramine.
f. "IDAM" means an alkali metal salt of IDA — e.g., the sodium or potassium salt of IDA.
g. "IDANa₂" means the sodium salt of IDA — i.e., H-N(CH₂COONa)₂-and "IDAK₂" means the potassium salt of IDA.

"Torr" means mm of mercury absolute, i.e., 760 Torr is one atmosphere.

"Percent yield" is a dimensionless number.

As used herein "psig" means pounds per square inch gauge pressure.

As used herein "⅛" × 10 '" means ⅛ inch by 10 feet and "⅛" × 20'" means ⅛ inch by 20 feet.

CH₂O and HCHO mean formaldehyde.

We claim:
1. A continuous process for preparing iminodiacetonitrile comprising:
   a. continuously preparing an aqueous reaction mixture of hexamethylenetetramine, formaldehyde, and HCN having a mole ratio of hexamethylenetetramine to formaldehyde to HCN of 1:1–2.2:6.9–8.6 in a continuous reaction zone by continuously feeding an aqueous hexamethylenetetramine solution having a temperature of 0°–80° C, an aqueous formaldehyde solution having a temperature of 0–80° C, and HCN having a temperature of 0°–25° C, into the continuous reaction zone, the pH of the aqueous reaction mixture being 5–10;

b. continuously preparing an aqueous system containing the iminodiacetonitrile by continuously passing the aqueous reaction mixture through the continuous reaction zone while maintaining the temperature within the continuous reaction zone at 50°–250° C, residence time in the continuous reaction zone being 0.05–20 minutes; and c. continuously recovering the iminodiacetonitrile exit the continuous reaction zone.

2. The process of claim 1 in which, the temperature within the continuous reaction zone is 120°–170° C.

3. The process of claim 1 in which the residence time in the continuous reaction zone is 0.1–5 minutes.

4. The process of claim 1 in which the pH of the aqueous reaction mixture is 6.5–9.5.

5. The process of claim 1 in which the aqueous system exit the continuous reaction zone is cooled to 0°–40° C to cause the iminodiacetonitrile to separate therefrom.

6. The process of claim 1 in which the mole ratio of hexamethylenetetramine to formaldehyde to HCN is 1:1.6–2.2:7.2–8.0

7. The process of claim 1 in which the mole ratio of hexamethylenetetramine to formaldehyde to HCN is 1:1.8:7.6.

8. The process of claim 1 in which the aqueous hexamethylenetetramine solution and the formaldehyde solution are admixed before being fed into the continuous reaction zone.

9. The process of claim 1 in which the formaldehyde solution, the HCN, and an acid stabilizer are admixed and fed into the continuous reaction zone, the acid stabilizer being present in an amount effective for forming an acid stabilizer aqueous admixture of formaldehyde and HCN.

* * * * *